United States Patent
Fang et al.

(10) Patent No.: US 11,090,012 B2
(45) Date of Patent: Aug. 17, 2021

(54) POSITRON EMISSION TOMOGRAPHY-MAGNETIC RESONANCE IMAGING APPARATUS

(71) Applicant: SHANGHAI UNITED IMAGING HEALTHCARE CO., LTD., Shanghai (CN)

(72) Inventors: Fuyi Fang, Shanghai (CN); Feng Xu, Shanghai (CN); Guanghe Wu, Shanghai (CN); Min Wu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 14 days.

(21) Appl. No.: 16/413,171

(22) Filed: May 15, 2019

(65) Prior Publication Data
US 2020/0237320 A1  Jul. 30, 2020

(30) Foreign Application Priority Data

Jan. 29, 2019 (CN) .......................... 201920155281.6
Feb. 1, 2019 (CN) .......................... 201910105242.X

(51) Int. Cl.
| | |
|---|---|
| A61B 6/03 | (2006.01) |
| G01R 33/48 | (2006.01) |
| A61B 5/055 | (2006.01) |
| A61B 6/00 | (2006.01) |
| A61B 6/10 | (2006.01) |
| A61B 5/00 | (2006.01) |
| G01T 1/16 | (2006.01) |

(52) U.S. Cl.
CPC .............. *A61B 6/037* (2013.01); *A61B 5/055* (2013.01); *A61B 6/102* (2013.01); *A61B 6/4417* (2013.01); *G01R 33/481* (2013.01); *A61B 5/0013* (2013.01); *A61B 5/0035* (2013.01); *A61B 5/0073* (2013.01); *G01T 1/1603* (2013.01)

(58) Field of Classification Search
CPC ....... A61B 6/037; A61B 5/055; A61B 6/4417; A61B 5/0035; A61B 5/0073; A61B 5/0013; A61B 6/102; A61B 6/4275; G01R 33/481; G01T 1/1603; G01T 1/2985
USPC .................................................... 250/363.04
See application file for complete search history.

(56) References Cited

U.S. PATENT DOCUMENTS

| | | | | |
|---|---|---|---|---|
| 7,667,457 B2 * | 2/2010 | Linz | ....................... | G01R 33/28 324/307 |
| 7,728,590 B2 * | 6/2010 | Eberler | .................. | A61B 5/055 324/318 |

(Continued)

FOREIGN PATENT DOCUMENTS

CN  205181369  *  4/2016

*Primary Examiner* — Mark R Gaworecki
(74) *Attorney, Agent, or Firm* — Metis IP LLC

(57) ABSTRACT

A PET-MR apparatus is provided. The PET-MR apparatus may include a first supporting component, a PET detector, a second supporting component, and a radio frequency (RF) coil. The first supporting component may have an inner surface and an outer surface. The PET detector may be supported on the outer surface of the first supporting component. The second supporting component may be at least partially surrounded by the first supporting component. The RF coil configured to generate or receive an RF signal may be supported on the second supporting component.

18 Claims, 8 Drawing Sheets

(56) References Cited

U.S. PATENT DOCUMENTS

| | | | |
|---|---|---|---|
| 9,041,397 B2 | 5/2015 | McBroom et al. | |
| 9,116,215 B2* | 8/2015 | Boskamp | G01R 33/025 |
| 9,188,651 B2 | 11/2015 | McBroom et al. | |
| 9,261,574 B2* | 2/2016 | Boskamp | G01R 33/34076 |
| 9,498,174 B2* | 11/2016 | Saha | G01R 33/34046 |
| 2009/0206836 A1* | 8/2009 | Eberler | A61B 5/055 |
| | | | 324/307 |
| 2010/0219347 A1* | 9/2010 | Schulz | G01T 1/1603 |
| | | | 250/363.04 |
| 2012/0253174 A1* | 10/2012 | Popescu | A61B 6/037 |
| | | | 600/411 |
| 2013/0193974 A1* | 8/2013 | McBroom | G01R 33/34 |
| | | | 324/322 |
| 2013/0234710 A1 | 9/2013 | Kanno et al. | |
| 2013/0284936 A1* | 10/2013 | McBroom | G01R 33/481 |
| | | | 250/363.03 |
| 2013/0293232 A1* | 11/2013 | Boskamp | G01R 33/422 |
| | | | 324/318 |
| 2014/0187909 A1* | 7/2014 | Saha | A61B 6/4417 |
| | | | 600/411 |
| 2015/0025358 A1* | 1/2015 | Emaci | A61B 5/0555 |
| | | | 600/411 |
| 2015/0045653 A1 | 2/2015 | Okamoto et al. | |
| 2018/0074144 A1* | 3/2018 | Dezorayev | A61B 5/055 |
| 2019/0310329 A1* | 10/2019 | Malik | G01R 33/3621 |

* cited by examiner

POSITRON EMISSION TOMOGRAPHY-MAGNETIC RESONANCE IMAGING APPARATUS

CROSS-REFERENCE TO RELATED APPLICATIONS

This application claims priority to Chinese Patent Application No. 201920155281.6 filed on Jan. 29, 2019, and Chinese Patent Application No. 201910105242.X filed on Feb. 1, 2019, the entire contents of each of which are hereby incorporated by reference.

TECHNICAL FIELD

This present disclosure relates to an imaging apparatus, and more particularly, relates to a positron emission tomography (PET)-magnetic resonance (MR) imaging apparatus.

BACKGROUND

Positron emission tomography (PET)-magnetic resonance (MR) is a hybrid imaging technique that incorporates both MR (e.g., a soft tissue morphological imaging technique) and PET (e.g., a functional imaging technique). In a conventional PET-MR imaging apparatus, components of a PET imaging apparatus (e.g., one or more PET detectors) and components of an MR imaging apparatus (e.g., an RF coil, a main magnet, a gradient magnet) may be integrated. For example, a PET detector may be mounted on an outer surface of a supporting component (e.g., a cylindrical supporting component), and an RF coil may be mounted on an inner surface of the supporting component.

However, due to the combination of the PET detector and the RF coil on the same supporting component, it is difficult to disassemble and/or assemble the PET detector and the RF coil, which may lead to a great maintenance difficulty and/or a high maintenance cost. In addition, the PET detector supported by the supporting component may be positioned in an accommodating region formed by a magnet coil (e.g., a main magnet, a gradient magnet) of the MR system. During the assembly of the PET detector, the PET detector may collide with an inner surface of the magnet coil, which may damage the PET detector or the magnet coil.

Therefore, it is desirable to provide a PET-MR imaging apparatus that may allow the PET detector and the RF coil to be separately assembled and also guarantee the safety of the PET detector during installation.

SUMMARY

According to an aspect of the present disclosure, a PET-MR apparatus is provided. The PET-MR apparatus may include a first supporting component, a PET detector, a second supporting component, and a radio frequency (RF) coil. The first supporting component may have an inner surface and an outer surface. The PET detector may be supported on the outer surface of the first supporting component. The second supporting component may be at least partially surrounded by the first supporting component. The RF coil configured to generate or receive an RF signal may be supported on the second supporting component.

In some embodiments, the MR-PET apparatus may include a magnetic coil formed around the outer surface of the first supporting component. The magnetic coil may include a main magnetic coil and a gradient magnetic coil.

In some embodiments, the RF coil may be attached to an outer surface of the second supporting component.

In some embodiments, the PET detector may be mounted on the outer surface of the first supporting component via a fastener.

In some embodiments, the first supporting component may be made of carbon fiber or glass fiber.

In some embodiments, the MR-PET apparatus may include a signal shielding component placed between the PET detector and the RF coil. The signal shielding component may be configured to shield the PET detector from at least part of the RF signal.

In some embodiments, the second supporting component may be removably connected to the inner surface of the first supporting component.

In some embodiments, the PET detector may include a detection unit and at least one mounting base. The detection unit may include a first proximal surface and a first distal surface with respect to the outer surface of the first supporting component. The at least one mounting base may be configured to mount the detection unit on the first supporting component. The at least one mounting base may include a second proximal surface and a second distal surface with respect to the outer surface of the first supporting component. The second distal surface of the at least one mounting base may be more distant from the outer surface of the first supporting component than the first distal surface of the detection unit.

In some embodiments, the first distal surface of the detection unit and the second distal surface of the at least one mounting base may be flat surfaces.

In some embodiments, the detection unit and the at least one mounting base may be an integral body.

In some embodiments, each of the at least one mounting base may be removably connected to the detection unit.

In some embodiments, the detection unit may include a detection component and a third supporting component. The third supporting component may be configured to support the detection component. The third supporting component and the at least one mounting base may be an integral body.

In some embodiments, each of the at least one mounting base may be removably connected to the third supporting component.

In some embodiments, each of the at least one mounting base may include a mounting hole. The each of the at least one mounting base may be mounted on the first supporting component via the mounting hole and a connection component passing through the mounting hole.

In some embodiments, each of the at least one mounting base may include a positioning hole penetrating through the mounting base in a direction perpendicular to the outer surface of the first supporting component.

In some embodiments, the PET-MR apparatus may include a groove at the second proximal surface of the at least one mounting base. The groove may be configured to accommodate at least one convex portion on the outer surface of the first supporting component.

In some embodiments, the PET detector may include a plurality of detection units. The plurality of detection units may be circumferentially arranged on the outer surface of the first supporting component to form a ring shape.

In some embodiments, the at least one mounting base may include an end ring. The end ring may include an inner edge where at least one detection unit of the plurality of detection units is joined to the end ring. The end ring may include an outer edge opposite to the inner edge and distal from the at least one detection unit.

According to another aspect of the present disclosure, a PET-MR apparatus is provided. The PET-MR apparatus may include a first supporting component and a PET detector. The first supporting component may have an inner surface and an outer surface. The PET detector may be supported on the outer surface of the first supporting component. The PET detector may include a detection unit and at least one mounting base. The detection unit may include a first proximal surface and a first distal surface with respect to the outer surface of the first supporting component. The at least one mounting base may be configured to mount the detection unit on the first supporting component. The at least one mounting base may include a second proximal surface and a second distal surface with respect to the outer surface of the first supporting component. The second distal surface of the at least one mounting base may be more distant from the outer surface of the first supporting component than the first distal surface of the detection unit.

In some embodiments, the PET-MR apparatus may include a magnetic coil. The magnetic coil may include a main magnetic coil and a gradient magnetic coil. The magnetic coil may form an accommodating region. The first supporting component may be positioned in the accommodating region. A gap may be formed between the second distal surface of the at least one mounting base and the magnetic coil.

In some embodiments, the first distal surface of the detection unit and the second distal surface of the at least one mounting base may be flat surfaces.

In some embodiments, the detection unit and the at least one mounting base may be an integral body.

In some embodiments, each of the at least one mounting base may be removably connected to the detection unit.

In some embodiments, the detection unit may include a detection component and a third supporting component. The third supporting component may be configured to support the detection component. The third supporting component and the at least one mounting base may be an integral body.

In some embodiments, each of the at least one mounting base may be removably connected to the third supporting component.

In some embodiments, each of the at least one mounting base may include a mounting hole. The each of the at least one mounting base may be mounted on the first supporting component via the mounting hole and a connection component passing through the mounting hole.

In some embodiments, each of the at least one mounting base may include a positioning hole penetrating through the mounting base in a direction perpendicular to the outer surface of the first supporting component.

In some embodiments, the PET-MR apparatus may include a groove at the second proximal surface of the at least one mounting base. The groove may be configured to accommodate at least one convex portion on the outer surface of the first supporting component.

In some embodiments, the PET detector may include a plurality of detection units. The plurality of detection units may be circumferentially arranged on the outer surface of the first supporting component to form a ring shape.

In some embodiments, the at least one mounting base may include an end ring. The end ring may include an inner edge where at least one detection unit of the plurality of detection units is joined to the end ring. The end ring may include an outer edge opposite to the inner edge and distal from the at least one detection unit.

In some embodiments, the PET-MR apparatus may include a second supporting component and a radio frequency (RF) coil. The second supporting component may be at least partially surrounded by the first supporting component. The radio frequency (RF) coil may be supported on the second supporting component. The RF coil may be configured to generate or receive an RF signal.

In some embodiments, the RF coil may be attached to an outer surface of the second supporting component.

In some embodiments, the PET detector may be mounted on the outer surface of the first supporting component via a fastener.

In some embodiments, the first supporting component may be made of carbon fiber or glass fiber.

In some embodiments, the PET-MR apparatus may include a signal shielding component placed between the PET detector and the RF coil. The signal shielding component may be configured to shield the PET detector from at least part of the RF signal.

In some embodiments, the second supporting component may be removably connected to the inner surface of the first supporting component.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
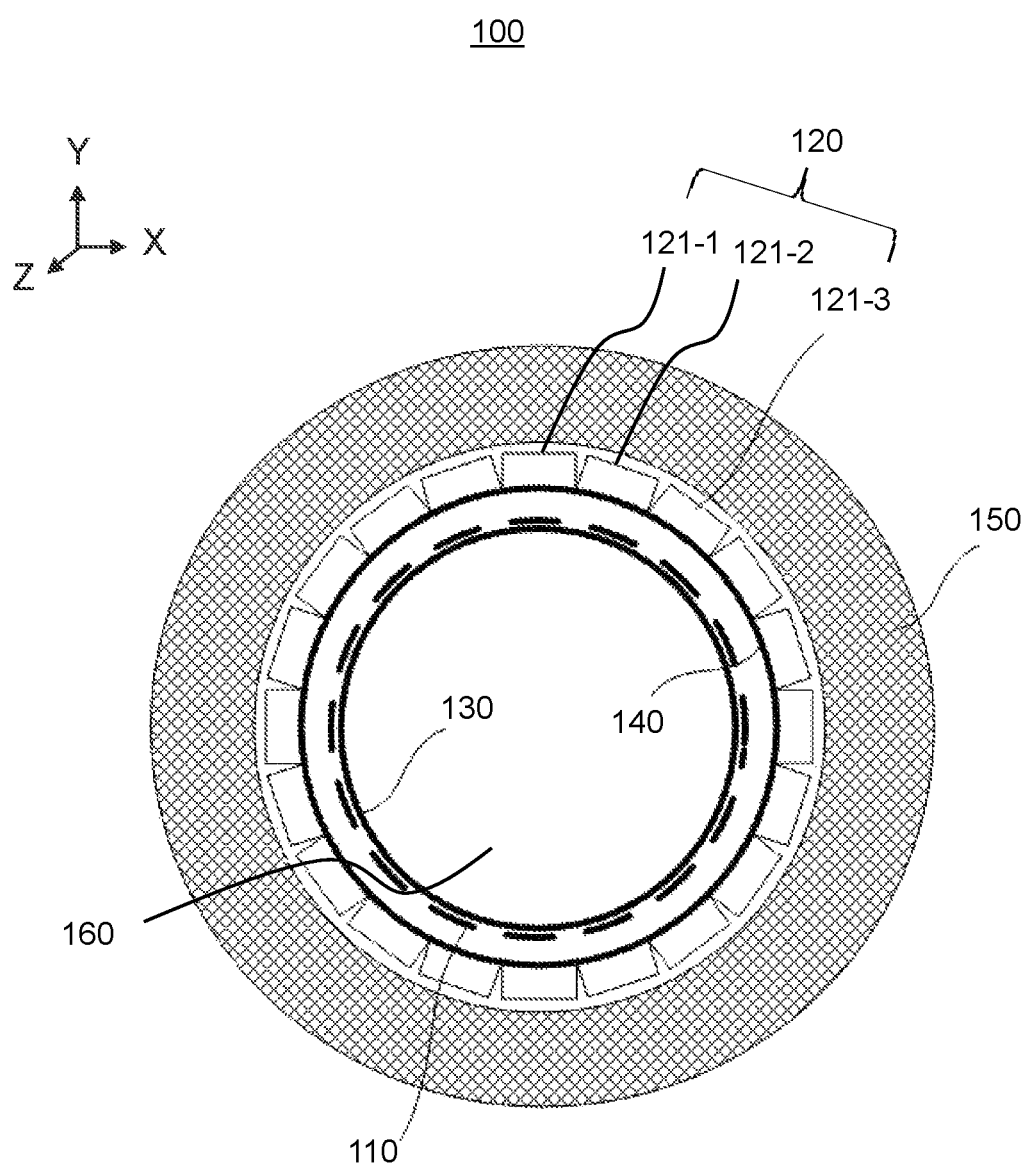
FIG. 1 is a cross-sectional view of an exemplary PET-MR apparatus according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the terms "hole," "surface," "groove," "ring," etc., when used in this disclosure, refer to one or more parts with one or more specific purposes. However, a structure that may perform a same or similar function compared to a part exemplified above or referred to elsewhere in the present disclosure may be named differently from the present disclosure.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

It will be understood that an "inner surface" may refer to a surface that is close to or faces a scanned object and an "outer surface" may refer to a surface that is away from or opposite to a scanned object.

Spatial and functional relationships between elements (for example, between layers) are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

It should also be understood that terms such as "top," "bottom," "upper," "lower," "vertical," "lateral" "above," "below," "upward(s)," "downward(s)," "left-hand side," "right-hand side," "horizontal," and other such spatial reference terms are used in a relative sense to describe the positions or orientations of certain surfaces/parts/components of the PET-MR apparatus with respect to other such features of the PET-MR apparatus when the PET-MR apparatus is in a normal operating position and may change if the position or orientation of the PET-MR apparatus changes.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

An aspect of the present disclosure relates to a PET-MR apparatus. The PET-MR apparatus may include a first supporting component, a PET detector, a second supporting component, and a radio frequency (RF) coil. The first supporting component may have an inner surface and an outer surface. The PET detector may be supported on the outer surface of the first supporting component. The second supporting component may be at least partially surrounded by the first supporting component. The RF coil configured to generate or receive an RF signal may be supported on the second supporting component. Accordingly, as supported by different supporting components, the RF coil and the PET detector of the PET-MR apparatus disclosed in the present disclosure may be separately assembled and/or disassembled, which may make the maintenance of the PET-MR apparatus more convenient.

In some embodiments, the PET detector may include a detection unit and at least one mounting base. The detection unit may include a first proximal surface and a first distal surface with respect to the outer surface of the first supporting component. The at least one mounting base may be configured to mount the detection unit on the first supporting component. The at least one mounting base may include a second proximal surface and a second distal surface with respect to the outer surface of the first supporting component. The second distal surface of the at least one mounting base may be more distant from the outer surface of the first supporting component than the first distal surface of the detection unit. Accordingly, during the assembly of the PET detector, the PET detector may be protected from being colliding with an inner surface of the magnet coil surrounding the PET detector due to the existence of the at least one mounting base, which may protect the PET detector.

FIG. 1 is a cross-sectional view of an exemplary PET-MR apparatus according to some embodiments of the present disclosure. In some embodiments, the PET-MR apparatus 100 may be an apparatus for generating an MR image and/or a PET image of an object. The MR image and/or the PET image may be generated individually or concurrently. The object may include a biological object and/or a non-biological object. The biological object may include a human being, an animal, a plant, or a portion thereof (e.g., a cell, a tissue, an organ, etc.). The non-biological object may include a radioactive ore, an antique, etc. In the present disclosure, "object" and "subject" are used interchangeably. As shown in FIG. 1, the PET-MR apparatus 100 may include an RF coil 110, a PET detector 120, a second supporting component 130, a first supporting component 140, and a magnetic coil 150.

The RF coil 110 may emit radiofrequency (RF) pulses (or RF signals) to and/or receive RF signals from an object being scanned. As used herein, an RF pulse may include an excitation RF pulse and a refocusing RF pulse. The RF coil 110 may include a quotient difference (QD) orthogonal coil and/or a phase-array coil. In some embodiments, the RF coil 110 may include a plurality of different types of RF coils. The different types of RF coils 110 may be used for the scanning of different parts of the object. For example, the different types of RF coils 110 may include a head coil specialized for the scanning of the head of the object, a knee joint coil specialized for the scanning of a knee joint of the object, etc. The RF coil 110 may include a volume coil and/or a local coil. For example, the volume coil may include a dipole coil, a birdcage coil, a transverse electromagnetic coil, a loop coil, a surface coil, etc. The local coil may include a solenoid coil, a saddle coil, a flexible coil, etc.

The PET detector 120 may be configured to detect signals, for example, attenuated radioactive rays, radiation events, etc. For example, the signals may be gamma photons emitted by the object. In particular, a radioactive tracer (e.g., fluorine-18) may be introduced into the object to be scanned. The radioactive tracer may decay and emit positrons. The positrons may encounter with electrons of the object and produce a pair of annihilation photons (e.g., gamma photons). Merely by way of example, the crystals of the PET detector 120 may generate an optical signal in response to the detected signals. The optical signal may be converted to an electric signal by a photoelectric converter. A PET image may be generated based on the electric signal.

In some embodiments, the size of the PET detector 120 in a circumferential direction of the PET-MR apparatus 100 may be larger than that of the RF coil 110. That is, the field of view of the PET imaging may be larger than the field of view of the MR imaging. In some embodiments, the field of view of the PET imaging may be equal to the field of view of the MR imaging.

In some embodiments, the PET detector 120 may include a plurality of detection units (e.g., a detection unit 121-1, a detection unit 121-2, a detection unit 121-3). In some embodiments, each detection unit may include a first proximal surface and a first distal surface with respect to the outer surface of the first supporting component 140. The plurality of detection units may be arranged around a circumferential direction of the first supporting component 140. The arrangement of the plurality of detection units may correspond to the shape of the first supporting component 140. For example, the first supporting component 140 may have a ring shape and the detection units may be uniformly arranged around the outer surface of the first supporting component 140 as a detection ring (as shown in FIG. 1). In some embodiments, the plurality of detection units may form a plurality of detection rings arranged around the outer surface of the first supporting component 140 along the Z direction (i.e., the longitudinal direction) of the PET-MR apparatus 100. Similarly, the detection units may be arranged around an arc, a rectangle, a triangle, or a curved array, etc., depending on the shape of the supporting component 140.

In some embodiments, the PET detector 120 may further include at least one mounting base (not shown in FIG. 1) configured to mount the detection units on the first supporting component 140. For example, two mounting bases may be configured on two outermost ends of the detection units, respectively, along the Z direction. As another example, the at least one mounting base may be configured on the first distal surface of a detection unit. The at least one mounting base may include a second proximal surface and a second distal surface with respect to the outer surface of the first supporting component 140. In some embodiments, the second distal surface of the at least one mounting base may be more distant from the outer surface of the first supporting component 140 than the first distal surfaces of the detection units. More descriptions of the detection units and the mounting bases may be found elsewhere in the present disclosure (e.g., FIGS. 6, 7, 8, and descriptions thereof).

In some embodiments, the arrangement of the at least one mounting base may correspond to the arrangement of the plurality of detection units. For example, the plurality of detection units may have a ring shape and thus the at least one mounting base may include one or more end rings along the Z direction. The end ring may include an inner edge where the outermost detection unit(s) are joined to the end ring. The end ring may include an outer edge opposite to the inner edge and distal from the detection units. In some embodiments, the diameter of the end ring may be greater than that of the detection ring. Therefore, during the assembly of the PET detector 120 on the first supporting component 140, the detection units of the PET detector 120 may be protected from being colliding with an inner surface of the magnet coil 150 due to the existence of the end ring(s), which may guarantee the normal use and the detection accuracy of the PET detector 120.

The magnetic coil 150 may include a main magnetic coil and a gradient magnetic coil. The main magnetic coil may generate a main magnetic field in a detection region 160. The main magnetic coil may be of various types including, for example, a permanent magnet, a superconducting electromagnet, a resistive electromagnet, etc. The main magnetic coil may have any magnetic field intensity, for example, 0.2 Tesla, 0.5 Tesla, 1.0 Tesla, 1.5 Tesla, and 3.0 Tesla.

The gradient magnet may generate magnetic field gradients to the main magnetic field in the X, Y, and/or Z directions (or axes). In some embodiments, the gradient magnet may include an X-direction (or axis) coil, a Y-direction (or axis) coil, a Z-direction (or axis) coil, etc. For example, the Z-direction coil may be designed based on a circular (Maxwell) coil configuration, while the X-direction coil and the Y-direction coil may be designed based on the saddle (Golay) coil configuration.

The first supporting component 140 (also referred to as a PET supporting component) may be configured to support one or more components of the PET-MR apparatus 100, such as the PET detector 120. In some embodiments, the PET detector 120 may be supported on an outer surface of the first supporting component 140. More descriptions of the first supporting component 140 may be found elsewhere in the present disclosure (e.g., FIGS. 3, 4, 5, and descriptions thereof).

The second supporting component 130 (also referred to as an RF coil supporting component) may be configured to support one or more components of the PET-MR apparatus 100, such as the RF coil 110. The second supporting component 130 may be at least partially surrounded by the first supporting component 140. In some embodiments, the second supporting component 130 may be coaxial with the first supporting component 140. In some embodiments, the RF coil 110 may be supported on an inner surface or an outer surface of the second supporting component 130. More descriptions of the second supporting component 130 may be found elsewhere in the present disclosure (e.g., FIGS. 3, 4, 5, and descriptions thereof).

In some embodiments, the inner surface of the second supporting component 130 may form the detection region 160 (or referred to as a detection channel, a scanning channel, or a scanning space). The object to be scanned may be placed on a scanning table (not shown in FIG. 1) and moved along the Z-direction to a desired position in the detection region 160 and be scanned (e.g., undergoing an MR scan and/or a PET scan).

In some embodiments, the magnetic coil 150 may be formed around the outer surface of the first supporting component 140. In some embodiments, the magnetic coil 150 may form an accommodating region. The first supporting component 140 may be positioned in the accommodating region. In some embodiments, the first supporting component 140 may be connected to an inner surface of the magnetic coil 150 via a holder or a fastener (e.g., a nail, a screw, a nut).

In some embodiments, the second supporting component 130 may be removably connected to the first supporting component 140. In some embodiments, the second supporting component 130 may be mechanically connected to the first supporting component via a fastener (e.g., a nail, a screw, a nut). For example, screw threads may be configured in relative positions of the first supporting component 140 and the second supporting component 130. The second supporting component 130 may be mechanically connected to the first supporting component via a screw rod penetrating through the screw threads. In some embodiments, a sliding track may be arranged between the first supporting component 140 and the second supporting component 130. The first supporting component 140 may slide along the sliding track to be removed from or installed on the second supporting component 130.

In some embodiments, the second supporting component 130 may be connected to the inner surface of the magnetic coil 150 directly. For example, the length of the second supporting component 130 along the Z direction may be greater than that of the first supporting component 140. Two ends of the second supporting component 130 may extend from the two ends of the first supporting component 140, respectively. The two ends of the second supporting component 130 may be directly connected to the inner surface of the magnetic coil 150 via a fastener (e.g., a nail, a screw, a nut).

In some embodiments, the PET-MR apparatus 100 may further include a signal shielding component placed between the PET detector 120 and the RF coil 110. The signal shielding component may be configured to shield the PET detector 120 from at least part of RF signals generated by the RF coil 110. For example, the signal shielding component may eliminate or reduce an interference (e.g., a coupling) between the RF coil 110 and the PET detector 120. In some embodiments, the signal shielding component may be arranged on the inner surface of the first supporting component 140. In some embodiments, the emission efficiency of the RF coil 110 may be related to the distance between the signal shielding component and the RF coil 110. For example, the greater the distance between the signal shielding component and the RF coil 110 (e.g., the radial distance), the higher the emission efficiency of the RF coil 110 can be. In some occasions, the thickness of the first supporting component 140 (i.e., the radial distance between the outer surface and the inner surface of the first supporting component 140) may be decreased to increase the distance between the signal shielding component and the RF coil 110, thus improving the emission efficiency of the RF coil 110.

In some embodiments, the signal shielding component may be made of electrically conductive material. Suitable electrically conductive materials may include a metal, a metal oxide, an alloy, rubber, graphite, a semiconductor, a composite polymer, or the like, or any combination thereof. The signal shielding component may have any suitable two-dimensional (2D) or three-dimensional (3D) configuration. For example, the signal shielding component may have the configuration of a film, a mesh, or the like, or any combination thereof. Specifically, the signal shielding component may be a metal film (e.g., a copper film), a metal plate, or the like. Alternatively, the signal shielding component may be a metal mesh.

In some embodiments, the signal shielding component (e.g., a conductive metal film) may be attached to the inner surface of the first supporting component 140 by any suitable technique, e.g., spin coating, dip coating, screen printing, transfer coating, sputtering, physical vapor deposition, chemical vapor deposition, or the like, or any combination thereof. In some embodiments, the signal shielding component (e.g., a metal mesh) may be assembled onto the inner surface of the first supporting component 140 via an adhesive.

It should be noted that the PET-MR apparatus 100 shown in FIG. 1 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the PET-MR apparatus 100 may further include a gantry (not shown in FIG. 1), configured to support one or more components of the PET-MR apparatus 100 (e.g., the RF coil 110, the PET detector 120, the second supporting component 130, the first supporting component 140, the magnetic coil 150, the signal shielding component).

Figure 2:
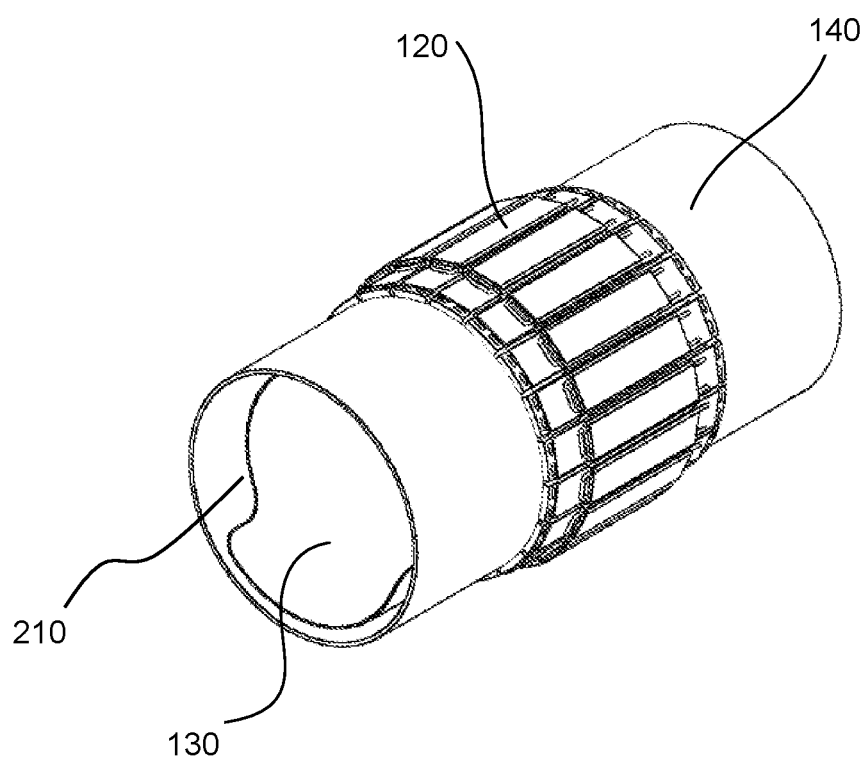
FIG. 2 is a perspective view of an exemplary connection structure of a first supporting component and a second supporting component according to some embodiments of the present disclosure.
Figure 3:
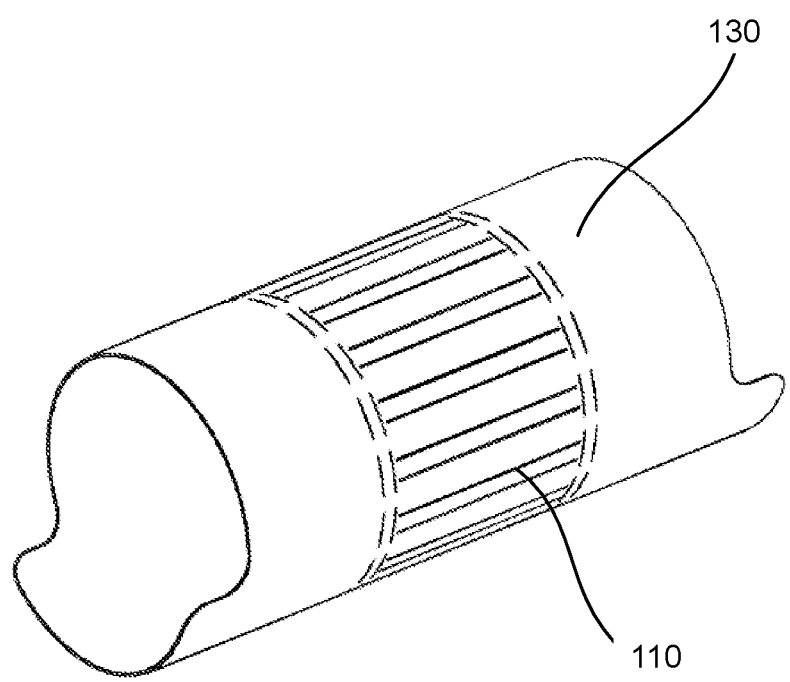
FIG. 3 is a perspective view of an exemplary connection structure of a second supporting component and an RF coil according to some embodiments of the present disclosure.
Figure 4:
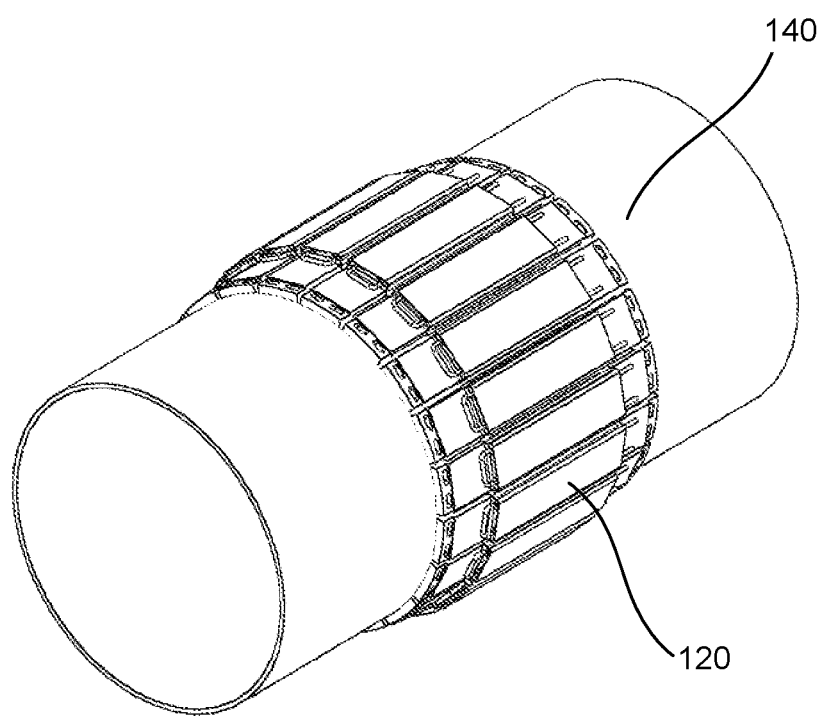
FIG. 4 is a perspective view of an exemplary connection structure of a first supporting component and a PET detector according to some embodiments of the present disclosure.

FIG. 2 is a perspective view of an exemplary connection structure of a first supporting component and a second supporting component according to some embodiments of the present disclosure. FIG. 3 is a perspective view of an exemplary connection structure of a second supporting component and an RF coil according to some embodiments of the present disclosure. FIG. 4 is a perspective view of an exemplary connection structure of a first supporting component and a PET detector according to some embodiments of the present disclosure.

As shown in FIG. 2, the first supporting component 140 and the second supporting component 130 may both have a cylindrical structure. The diameter of the first supporting component 140 may be greater than that of the second supporting component 130. The second supporting component 130 may be at least partially surrounded by the first supporting component 140. In some embodiments, a notch 210 may be formed at an end of the second supporting component 130. The notch 210 may be configured to match the shape of a scanning table (not shown in FIG. 2).

In some embodiments, the RF coil 110 may be supported on the second supporting component 130, as shown in FIG. 3. For example, the RF coil 110 may be supported on an inner surface or an outer surface of the second supporting component 130. In some embodiments, the RF coil 110 may be attached on the second supporting component 130 via a chemical component (e.g., an adhesive), a fastener (e.g., a nail, a screw, a nut), or the like, or any combination thereof.

In some embodiments, the PET detector 120 may be supported on the outer surface of the first supporting component 140, as shown in FIGS. 2 and 4. In some embodiments, the PET detector 120 may be mounted on the first supporting component 140 via a chemical component (e.g., an adhesive), a fastener (e.g., a nail, a screw, a nut), a mounting base, or the like, or any combination thereof. In some embodiments, the PET detector 120 may be located at a relatively long distance from the RF coil 110, which may be advantageous for reducing the electromagnetic field interference between the RF coil 110 and the PET detector 120. In this situation, the emission efficiency of the RF coil 110 can be set to be relatively high.

According to the PET-MR apparatus 100 disclosed in the present disclosure, the RF coil 110 and the PET detector 120 may be fixed in the PET-MR apparatus by the second supporting component 130 and the first supporting component 140, respectively. By doing so, on one hand, the combined assembly of the RF coil 110 and the PET detector 120 may be realized. On the other hand, the RF coil 110 and the PET detector 120 may be separately assembled and/or disassembled, so that the RF coil 110 and/or the PET detector 120 may be maintained separately. For example, if the RF coil 110 breaks down, an operator may only need to disassemble the RF coil 110 from the PET-MR apparatus 100 by detaching the second supporting component 130 from the PET-MR apparatus 100, leaving the PET detector 120 in its place in the PET-MR apparatus 100. If the PET detector 120 breaks down, an operator may only need to disassemble the PET detector 120 from the PET-MR apparatus 100 by detaching the first supporting component 140 from the PET-MR apparatus 100, leaving the RF coil 110 in its place in the PET-MR apparatus 100. As such, the maintenance of the PET-MR apparatus may be simple and convenient, and the maintenance cost may be saved.

The first supporting component 140 and/or the second supporting component 130 may be made of any suitable material that has high strength and/or stability to provide a stable support for the PET detector 120 and the RF coil 110. In some embodiments, since the weight of the PET detector 120 is greater than that of the RF coil 110, the strength of the first supporting component 140 may be higher than that of the second supporting component 130. In some embodiments, the first supporting component 140 and the second supporting component 130 may be made of a same material. The thickness of the second supporting component 130 may be less than the thickness of the first supporting component 140. In some embodiments, the first supporting component 140 and the second supporting component 130 may be made of different materials.

In some embodiments, the thickness of the first supporting component 140 may relate to the material of the first supporting component 140. In some embodiments, the first supporting component 140 may be made of electrically conductive material. For example, the first supporting component 140 may be made of carbon fiber. The carbon fiber may have a good electromagnetic field shielding effect, which may reduce the interference between the RF coil 110 and the PET detector 120. In this situation, no additional signal shielding component is needed in the PET-MR apparatus 100, which may reduce the complexity of the PET-MR apparatus 100. In this situation, the thickness of the first supporting component 140 may be in a range of 4 mm to 6 mm. In some embodiments, the first supporting component 140 may be made of an insulation material. For example, the first supporting component 140 may be made of glass fiber. In this situation, a signal shielding component may be placed between the PET detector 120 and the RF coil 110. The signal shielding component may be configured to shield the PET detector from at least part of the RF signal. For example, the signal shielding component may be attached on the inner surface of the first supporting component 140. More descriptions of the signal shielding component may be found elsewhere in the present disclosure (e.g., FIGS. 1, 5, and descriptions thereof). In this situation, the thickness of the first supporting component 140 may be in a range of 6 mm to 10 mm.

In some embodiments, the second supporting component 130 may be made of an insulation material. For example, the second supporting component 130 may be made of glass fiber. In this situation, the thickness of the second supporting component 130 may be less than that of the first supporting component 140. For example, the thickness of the second supporting component may be in a range of 3 mm to 5 mm.

It should be noted that the first supporting component 140 and the second supporting component 130 shown in FIGS. 2, 3, and 4 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 5:
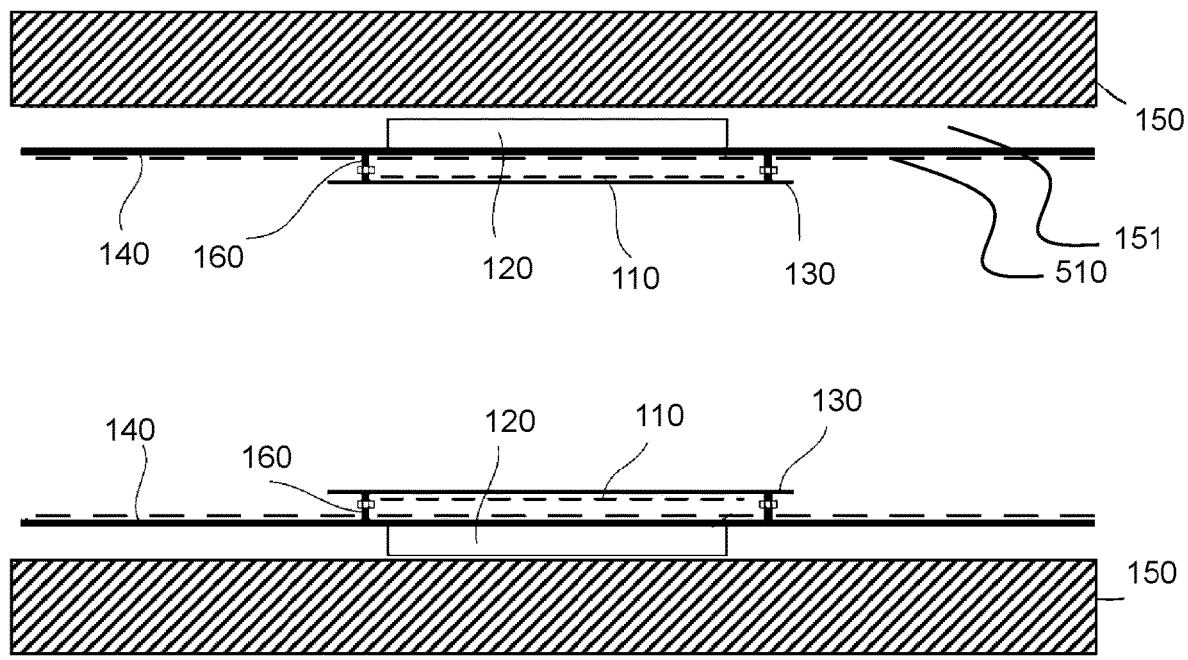
FIG. 5 is a sectional view of an exemplary PET-MR apparatus viewed from a direction perpendicular to the longitudinal axis according to some embodiments of the present disclosure.

FIG. 5 is a sectional view of an exemplary PET-MR apparatus 500 viewed from a direction perpendicular to the longitudinal axis according to some embodiments of the present disclosure. In some embodiments, the PET-MR apparatus 500 may be same as or similar to the PET-MR apparatus 100, or a portion thereof.

As shown in FIG. 5, the PET-MR apparatus 500 may include the RF coil 110, the PET detector 120, the second supporting component 130, the first supporting component 140, the magnetic coil 150, and a signal shielding component 510. The magnetic coil 150 may be formed around an outer surface of the first supporting component 140. In some embodiments, the magnetic coil 150 may form an accommodating region 151. The first supporting component 140 may be positioned in the accommodating region 151. The PET detector 120 may be supported on the outer surface of the first supporting component 140. More descriptions of the connection between the PET detector 120 and the first supporting component 140 may be found elsewhere in the present disclosure (e.g., FIGS. 6, 7, 8, and descriptions thereof).

The second supporting component 130 may be at least partially surrounded by the first supporting component 140. The RF coil 110 may be supported on an outer surface of the second supporting component 140. In some embodiments, the second supporting component 130 may also be used as an insulation component between the RF coil 110 and a patient to be scanned, which may isolate the patient and the RF coil 110, and improve the safety performance of the PET-MR apparatus 500.

In some embodiments, the second supporting component 130 may be removably connected to the first supporting component 140. For example, the second supporting component 130 may be connected to the inner surface of the first supporting component 140 via a fastener 160. In some embodiment, in order to ensure the emission efficiency of the RF coil 110, save the installation space, and provide a large accommodating space for the patient, the spacing between the first supporting component 140 and the second supporting component 130 along the radial direction of the PET-MR apparatus 500 may be in a range of 15 mm to 30 mm.

In some embodiments, the PET detector 120 and the RF coil 110 may be configured along a radial direction of the PET-MR apparatus 500. The PET detector 120 and the RF coil 110 may be spaced apart from each other by providing the first supporting component 140, the second supporting component 130, and the fastener 160. Accordingly, the influence of the heat of the PET detector 120 on the RF coil 110 may be reduced, and the influence of the heat of the RF coil 110 on the PET detector 120 may also be reduced.

In some embodiments, the signal shielding component 510 may be configured on the inner surface of the first supporting component 140. For example, the signal shielding component 510 may be a metal film or a metal mesh attached to the inner surface of the first supporting component 140.

It should be noted that the PET-MR apparatus 500 shown in FIG. 5 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 6:
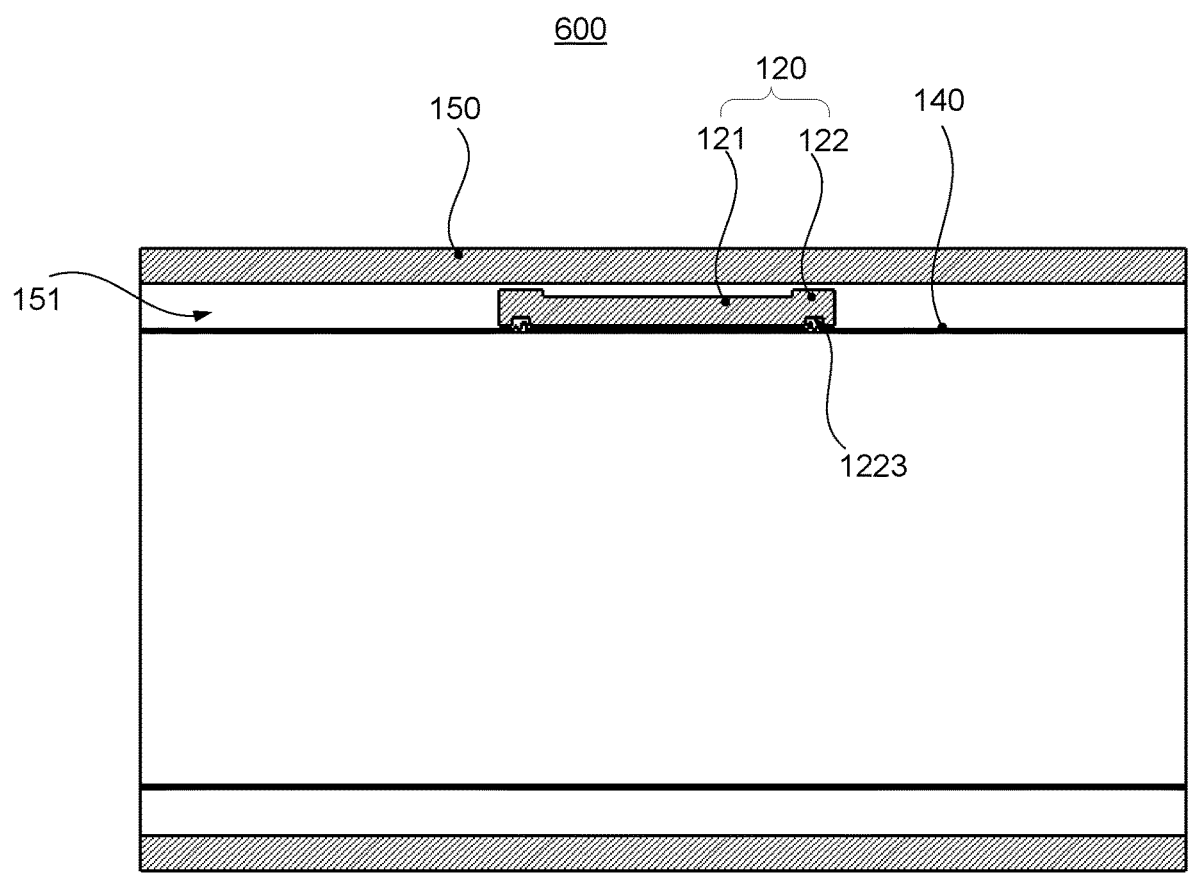
FIG. 6 is a sectional view of an exemplary PET-MR apparatus viewed from a direction perpendicular to the longitudinal axis according to some embodiments of the present disclosure.
Figure 7:
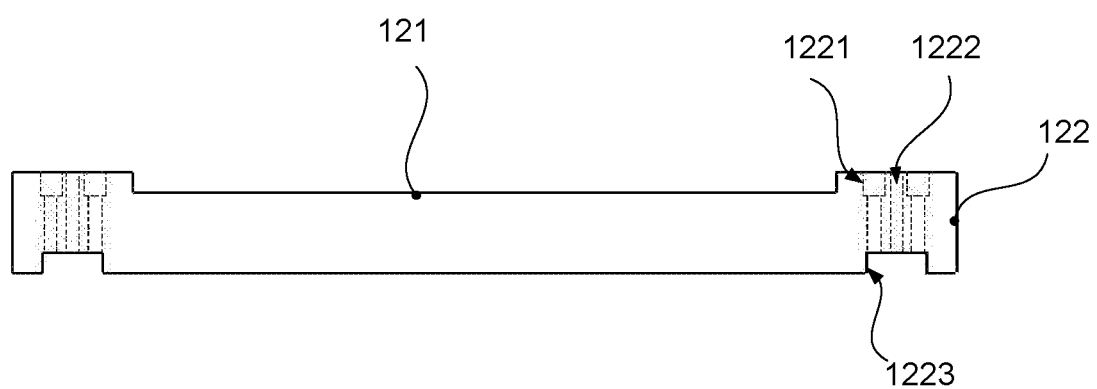
FIG. 7 is a sectional view of an exemplary PET detector according to some embodiments of the present disclosure.

FIG. 6 is a sectional view of an exemplary PET-MR apparatus 600 viewed from a direction perpendicular to the longitudinal axis according to some embodiments of the present disclosure. In some embodiments, the PET-MR apparatus 600 may be same as or similar to the PET-MR apparatus 100, the PET-MR apparatus 500, or a portion thereof. FIG. 7 is a sectional view of an exemplary PET detector 700 according to some embodiments of the present disclosure. In some embodiments, the PET detector 700 may be same as or similar to the PET detector 120, or a portion thereof.

As shown in FIG. 6, the PET detector 120 may include a detection unit 121 and at least one mounting base 122. In some embodiments, the detection unit 121 may include a detection component (not shown in FIG. 6) and a third supporting component (not shown in FIG. 6). The detection component may be configured to detect signals. In some embodiments, the detection component may include a crystal unit, a photoelectric conversion unit, an electronic circuit, or the like. The crystal unit, the photoelectric conversion unit, and the electronic circuit may be electrically connected with each other in sequence. The third supporting component may be configured to support the detection component. For example, the crystal unit and the photoelectric conversion unit may be mounted on a first side of the third supporting component close to the first supporting component 140, and the electronic circuit may be configured on a second side of the third supporting component away from the first supporting component 140. In some embodiments, the third supporting component may have a heat dissipation structure for dissipating heat and/or a cooling structure for cooling the detection component to ensure the working performance of the detection component. In some embodiments, the third supporting component and the at least one mounting base 122 may be an integral body. In some embodiments, the third supporting component may be removably connected to the at least one mounting base 122.

In some embodiments, the detection unit 121 may include a first proximal surface and a first distal surface with respect to the outer surface of the first supporting component 140. The at least one mounting base 122 may include a second proximal surface and a second distal surface with respect to the outer surface of the first supporting component 140. The second distal surface of the at least one mounting base 122 may be more distant from the outer surface of the first supporting component 140 than the first distal surface of the detection unit 121. Accordingly, a gap formed between the second distal surface of the at least one mounting base 122 and the inner surface of the magnetic coil 150 may be smaller than a gap formed between the first distal surface of the detection unit 121 and the inner surface of the magnetic coil 150.

In some embodiments, the first distal surface of the detection unit 121 may have any shape. For example, the first distal surface of the detection unit 121 may be flat. As another example, the first distal surface of the detection unit 121 may be curved, and parallel to the outer surface of the first supporting component 140. As still another example, the first distal surface of the detection unit 121 may be uneven. In this situation, the second distal surface of the at least one mounting base 122 may have any shape, as long as any point on the second distal surface of the at least one mounting base 122 is more distant from the outer surface of the first supporting component 140 than any point on the first distal surface of the detection unit 121.

In some embodiments, the second distal surface of the at least one mounting base 122 may have any shape. For example, the second distal surface of the at least one mounting base 122 may be flat. As another example, the second distal surface of the at least one mounting base 122 may be curved, and parallel to the outer surface of the first supporting component 140. As still another example, the second distal surface of the at least one mounting base 122 may be uneven. In this situation, the first distal surface of the detection unit 121 may have any shape, as long as any point on the second distal surface of the at least one mounting base 122 is more distant from the outer surface of the first supporting component 140 than any point on the first distal surface of the detection unit 121.

Therefore, during the assembly of the PET detector 120 supported on the first supporting component 140 in the accommodating region 151, the detection unit 121 of the PET detector 120 may be protected from being colliding with an inner surface of the magnet coil 150 by the at least one mounting base 122, which may guarantee the normal use and the detection accuracy of the PET detector 120.

In a conventional PET-MR apparatus, the PET detector may be mounted in a groove configured in the outer surface of a supporting component to protect the PET detector 120 from being squeezed or impacted during the assembly. The supporting component with the groove in its outer surface may have a relative large size (e.g., thickness) along the radial direction. In comparison, the PET-MR apparatus according to some embodiments of the present disclosure may mount the PET detector 120 on the first supporting component 140 having a relatively small thickness directly, without making the groove in the outer surface of the first supporting component 140. Therefore, the requirement for the thickness of the first supporting component 140 may be reduced, and the fabrication complexity and cost may be effectively reduced.

In some embodiments, the detection unit 121 and the at least one mounting base 122 may be an integral body. Accordingly, the connection between the detection unit 121 and the at least one mounting base 122 may be stable, which may avoid the risk of the detection unit 121 falling off from the at least one mounting base 122. In some embodiments, each of the at least one mounting base 122 may be removably connected to the detection unit 121. For example, the each of the at least one mounting base 122 may be removably connected to the detection unit 121 via a buckle structure (e.g., a hook and a slot). As another example, the each of the at least one mounting base 122 may be removably connected to the detection unit 121 via a fastener (e.g., a screw).

In some embodiments, the at least one mounting bases 122 may be configured on two ends of the detection unit 121 to mount the detection unit 121 on the first supporting component 140, as shown in FIGS. 6 and 7. In some embodiments, the each of the at least one mounting base 122 may be removably connected to the first supporting component 140. For example, the each of the at least one mounting base 122 may be connected to the first supporting component 140 via a chemical component (e.g., an adhesive), a fastener (e.g., a nail, a screw, a nut), or the like, or any combination thereof. Accordingly, the installation of the PET detector 120 and the first supporting component 140 may be realized by the detachable connection of the at least one mounting base 122 and the first supporting component 140. The connection structure of the at least one mounting base 122 and the first supporting component 140 may be simple, easy to design, and may not affect the PET detector 120 to receive signals.

In some embodiments, the mounting base 122 may include one or more mounting holes 1221, as shown in FIG. 7. The mounting base 122 may be mounted on the first supporting component 140 via the one or more mounting holes 1221 and one or more connection components passing through the one or more mounting holes 1221. In some embodiments, the mounting hole 1221 may penetrate through the mounting base 122 in a direction perpendicular to the outer surface of the first supporting component 140. In some embodiments, the connection component may include a screw, a bolt, a pin, or the like. By providing the mounting hole 1221 in the mounting base 122, and fixing the mounting base 122 on the first supporting component 140 via the connection component passing through the mounting hole 1221, the connection structure of the mounting base 122 and the first supporting component 140 may be simple, stable, and easy to assembly or disassembly.

In some embodiments, the mounting hole 1221 may include a countersink at the second distal surface of the at least one mounting base 122. By designing the mounting hole 1221 as the countersink, the connection component may fix the mounting base 122 on the first supporting component 140 without protruding from the mounting base 122, which may improve the overall aesthetics of the PET detector 120 configured on the first supporting component 140.

In some embodiments, the mounting base 122 may include a positioning hole 1222. The positioning hole 1222 may penetrate through the mounting base 122 in a direction perpendicular to the outer surface of the first supporting component 140. In some embodiments, a positioning pin (not shown in FIGS. 6, 7) may be configured on the first supporting component 140. Before the mounting base 122 is fixed on the first supporting component 140, the position of the mounting base 122 and the position of the first supporting component 140 may be aligned via the reception of the positioning pin by the positioning hole 1222, which may facilitate the positioning and the installation of the PET detector 120 on the first supporting component 140.

In some embodiments, a groove 1223 may be configured at the second proximal surface of the mounting base 122. The groove 1222 may be configured to accommodate at least one convex portion on the outer surface of the first supporting component 140. In some embodiments, the convex portion on the outer surface of the first supporting component 140 may include a process boss generated during the manufacturing process (e.g., an embedded process, an inlaid process) of the first supporting component 140. By designing the groove 1223 on the mounting base 122, the convex portion on the outer surface of the first supporting component 140 may be accommodated, so that the PET detector 120 may be mounted on the first supporting component 140 closely, which may save installation space.

Figure 8:
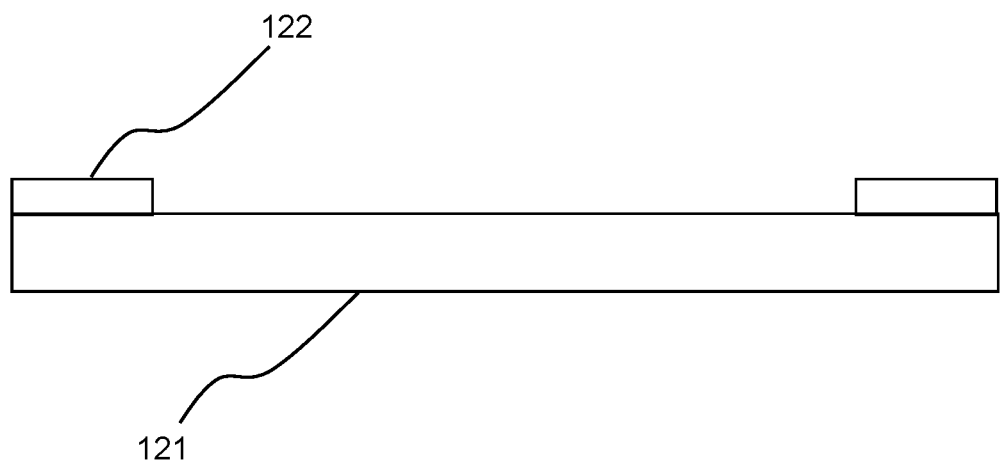
FIG. 8 is a sectional view of an exemplary PET detector according to some embodiments of the present disclosure.

FIG. 8 is a sectional view of an exemplary PET detector 800 according to some embodiments of the present disclosure. In some embodiments, the PET detector 800 may be same as or similar to the PET detector 120, or a portion thereof.

As shown in FIG. 8, the at least one mounting base 122 may be configured on the first distal surface of the detection unit 121, thus between the detection unit 121 and the magnet coil surrounding the detection unit 121. The detection unit 121 may be connected to the first supporting component 140 via a chemical component (e.g., an adhesive), a fastener (e.g., a nail, a screw, a nut), or the like, or any combination thereof. Therefore, the detection unit 121 of the PET detector 120 may be protected from being colliding with an inner surface of the magnet coil by the at least one mounting base 122, which may guarantee the normal use and the detection accuracy of the PET detector 120. The number of the at least one mounting base 122 may not be limiting. For example, besides two mounting bases 122 at the two ends of the detection unit 121, one or more mounting bases 122 may be positioned on other positions of the detection unit 121, e.g., a position between the two mounting bases 122 at the two ends of the detection unit 121.

In some embodiments, the PET detector may include a plurality of detection units 121. In some embodiments, the plurality of detection units 121 may be circumferentially arranged on the outer surface of the first supporting component to form a ring shape, as shown in FIG. 1. In some embodiments, the plurality of detection units 121 may form a plurality of detection rings arranged around the outer surface of the first supporting component along the Z direction (i.e., the longitudinal direction) of the PET-MR apparatus (e.g., the PET-MR apparatus 100, the PET-MR apparatus 600).

In some embodiments, the arrangement of the at least one mounting base 122 may correspond to the arrangement of the plurality of detection units 121. For example, the plurality of detection units 121 may have the ring shape and thus the at least one mounting base 122 may include one or more end rings along the Z direction. The end ring may include an inner edge where the outermost detection unit(s) in the Z direction are joined to the end ring. The end ring may include an outer edge opposite to the inner edge and distal from the detection units 121. In some embodiments, the outside diameter of the end ring may be greater than that of the detection ring. Therefore, during the assembly of the PET detector, the detection units 121 of the PET detector 120 may be protected from being colliding with an inner surface of the magnet coil due to the existence of the end ring(s), which may guarantee the normal use and the detection accuracy of the PET detector.

It should be noted that the PET-MR apparatus 600 shown in FIG. 6, the PET detector 700 shown in FIG. 7, and the PET detector 800 shown in FIG. 8 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A positron emission tomography-magnetic resonance (PET-MR) apparatus, comprising:
    a first supporting component having an inner surface and an outer surface;
    a magnetic coil formed around the outer surface of the first supporting component; and
    a PET detector supported on the outer surface of the first supporting component, wherein the PET detector includes:
        a detection unit including a first proximal surface and a first distal surface with respect to the outer surface of the first supporting component; and
        at least one mounting base configured to mount the detection unit on the first supporting component, the at least one mounting base including a second proximal surface and a second distal surface with respect to the outer surface of the first supporting component, the second distal surface of the at least one mounting base being more distant from the outer surface of the first supporting component than the first distal surface of the detection unit, a gap formed between the first distal surface of the detection unit and an inner surface of the magnetic coil being greater than a gap formed between the second distal surface of the at least one mounting base and the inner surface of the magnetic coil, such that the detection unit is protected from being colliding with the inner surface of the magnetic coil by the at least one mounting base.

2. The PET-MR apparatus of claim 1, wherein the magnetic coil includes a main magnetic coil and a gradient magnetic coil, the magnetic coil forms an accommodating region, the first supporting component being positioned in the accommodating region, and a gap being formed between the second distal surface of the at least one mounting base and the magnetic coil.

3. The PET-MR apparatus of claim 1, wherein the first distal surface of the detection unit and the second distal surface of the at least one mounting base are flat surfaces.

4. The PET-MR apparatus of claim 1, wherein the detection unit and the at least one mounting base is an integral body.

5. The PET-MR apparatus of claim 1, wherein each of the at least one mounting base is removably connected to the detection unit.

6. The PET-MR apparatus of claim 5, wherein the detection unit includes:
    a detection component; and
    a third supporting component configured to support the detection component, wherein the third supporting component and the at least one mounting base is an integral body.

7. The PET-MR apparatus of claim 6, wherein each of the at least one mounting base is removably connected to the third supporting component.

8. The PET-MR apparatus of claim 1, wherein each of the at least one mounting base includes a mounting hole, and the each of the at least one mounting base is mounted on the first supporting component via the mounting hole and a connection component passing through the mounting hole.

9. The PET-MR apparatus of claim 1, wherein each of the at least one mounting base includes a positioning hole penetrating through the mounting base in a direction perpendicular to the outer surface of the first supporting component.

10. The PET-MR apparatus of claim 1, further comprising:
    a groove at the second proximal surface of the at least one mounting base, the groove being configured to accommodate at least one convex portion on the outer surface of the first supporting component.

11. The PET-MR apparatus of claim 1, wherein the PET detector includes a plurality of detection units, the plurality of detection units being circumferentially arranged on the outer surface of the first supporting component to form a ring shape.

12. The PET-MR apparatus of claim 11, wherein the at least one mounting base includes an end ring, the end ring including an inner edge where at least one detection unit of the plurality of detection units is joined to the end ring, and the end ring includes an outer edge opposite to the inner edge and distal from the at least one detection unit.

13. The PET-MR apparatus of claim 1, further comprising:
 a second supporting component being at least partially surrounded by the first supporting component; and
 a radio frequency (RF) coil supported on the second supporting component, the RF coil being configured to generate or receive an RF signal.

14. The PET-MR apparatus of claim 13, wherein the RF coil is attached to an outer surface of the second supporting component.

15. The PET-MR apparatus of claim 13, wherein the PET detector is mounted on the outer surface of the first supporting component via a fastener.

16. The PET-MR apparatus of claim 13, wherein the first supporting component is made of carbon fiber or glass fiber.

17. The PET-MR apparatus of claim 13, further comprising:
 a signal shielding component placed between the PET detector and the RF coil, the signal shielding component being configured to shield the PET detector from at least part of the RF signal.

18. The PET-MR apparatus of claim 13, wherein the second supporting component is removably connected to the inner surface of the first supporting component.

* * * * *